(12) United States Patent
Kalota et al.

(10) Patent No.: US 7,750,187 B2
(45) Date of Patent: Jul. 6, 2010

(54) CRYSTALLIZATION METHOD FOR BENZPHETAMINE

(75) Inventors: Dennis J. Kalota, Fenton, MO (US); Keith G. Tomazi, Florissant, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 340 days.

(21) Appl. No.: 11/719,001

(22) PCT Filed: Nov. 2, 2005

(86) PCT No.: PCT/US2005/039448

§ 371 (c)(1), (2), (4) Date: May 10, 2007

(87) PCT Pub. No.: WO2006/060099

PCT Pub. Date: Jun. 8, 2006

(65) Prior Publication Data

US 2008/0262268 A1    Oct. 23, 2008

(51) Int. Cl.
*C07C 211/00* (2006.01)

(52) U.S. Cl. .................................... 564/305
(58) Field of Classification Search ............. None
See application file for complete search history.

(56) References Cited

U.S. PATENT DOCUMENTS

| | | | |
|---|---|---|---|
| 1,854,553 A | | 5/1926 | Livingston |
| 2,789,138 A | | 4/1957 | Heinzelman |
| 3,182,060 A | * | 5/1965 | Berchtold ............ 544/165 |
| 3,676,558 A | | 7/1972 | Hester, Jr. |
| 4,277,420 A | | 7/1981 | Koenig |
| 4,747,920 A | * | 5/1988 | Muralidhara et al. ...... 204/542 |
| 5,236,922 A | | 8/1993 | Lafon |
| 6,458,830 B1 | | 10/2002 | Owen et al. |
| 6,489,343 B2 | | 12/2002 | Pineiro et al. |

FOREIGN PATENT DOCUMENTS

WO    WO2006057778    *    6/2006

OTHER PUBLICATIONS

Chen C. et al. Organic Process Research and Development 2001, 5, 508-513.*

* cited by examiner

*Primary Examiner*—Daniel M Sullivan
*Assistant Examiner*—Clinton Brooks

(57) ABSTRACT

There is disclosed a method for the crystallization of benzphetamine hydrochloride from an organic medium by the steps of removing water from the system to a very low level and then reducing the temperature of the organic medium to provide crystallization of the acid salt. In the event that crystallization does not occur upon lowering the temperature of the medium, it has been discovered that gentle heating of the organic medium results in crystallization of the acid salt. It has also been discovered that higher temperature crystallization has been provided by removal of methamphetamine from the composition. The crystalline benzphetamine hydrochloride can then be isolated by typical liquid/solid separation means such as filtration or centrifugation.

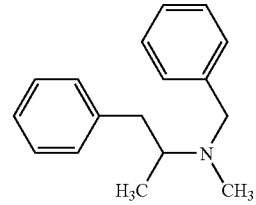

31 Claims, No Drawings

CRYSTALLIZATION METHOD FOR BENZPHETAMINE

BACKGROUND OF INVENTION

This invention relates to a method for purifying and crystallizing benzphetamine acid salt by means of a convenient process for inducing crystallization of the salt from a liquid organic medium.

The production of benzphetamine has been known for a considerable period of time and was disclosed in U.S. Pat. No. 2,789,138 to Heinzelman et al. The chemical name of the physioacitve material, benzphetamine, is d-N-methyl-N-benzyl-beta-phenylisopropylamine. According to that patent benzyl chloride is reacted with methamphetamine in the presence of a base, typically sodium carbonate. The reaction is typically carried out in a non-reactive organic medium such as benzene, toluene, xylene or the like. The product is recovered by mixing the reaction mixture with water, extracting with medium, and then fractionally distilling at temperatures of about 127° C. and at a pressure of 0.2 mm of mercury, then converting the benzphetamine to the hydrochloride by addition of hydrochloric acid. The thus produced acid salt, typically in the form of an oil, is crystallized from the medium by the addition of ether. Such purification process has several disadvantages including the exposure of the product to high temperatures, and the need for expensive vacuum pumps and a vacuum still to achieve the desired reduced pressure.

In organic chemistry it is common to provide purification and isolation procedures that involve such standard operations as refluxing, azeotropic distillation, liquid partitioning and crystallization. Such processes are demonstrated by U.S. Pat. Nos. 6,489,343 and 6,458,830. While these patents are not concerned with the product of concern herein, they are representative of the above noted procedures for purification and isolation of product. In U.S. Pat. No. 5,236,922, the preparation and isolation of 1-(aminophenyl)-2-aminopropaneone derivatives are disclosed. The product 1-(4-acetylamino-3-chlorophenyl)-2-chrolopropanone was recrystallized from toluene. In U.S. Pat. No. 4,277,420 ephedrine and pseudoephedrine precursors described as N-(1-aroyl-1-alkenylamides were recrystallized from toluene. In U.S. Pat. No. 1,854,553 the production of ethyl benzylaniline by reacting monethylaniline with benzyl chloride is disclosed. The product is recovered from toluene by distillation.

Typically, benzphetamine hydrochloride forms an oil in the current processes that then require vacuum distillation to separate the oil from the reaction medium and provide a material that can be crystallized. While methods described in the above noted U.S. Pat. No. 2,789,138 are considered the standard whereby benzphetamine hydrochloride is currently manufactured, there is needed a convenient method for providing crystalline benzphetamine hydrochloride directly from the reaction medium rather than isolating it by distillation followed by crystallization. Further, it has been found that water/medium extraction leads to the need for further purification. Therefore, a process is needed that provides for isolation of the product in crystalline form in a manner that eliminates as much as possible any water from the system.

SUMMARY OF INVENTION

In accordance with this invention a method for crystallization of benzphetamine acid salt, typically the hydrochloride salt, is provided wherein the acid salt is crystallized directly from an organic medium such as toluene. It has been discovered that benzphetamine acid salt does not crystallize unless water levels, both free and dissolved water, are reduced to surprisingly low levels. It has been found that even traces of water inhibit such crystallization and may cause impurities to be carried into the product that require removal to provide desirable product color. Accordingly in one aspect of this invention benzphetamine hydrochloride is crystallized by lowering water content to surprisingly low levels. Such removal is typically carried out by distillation means of various types. In another embodiment of the invention, water is removed from crude benzphetamine acid salt upon heating to a temperature above approximately 100° C.

There is now provided a multi-step process for the crystallization of the benzphetamine acid salt out of the reaction mass whereby water is first removed from the reaction mass by typical means such as by distillation, absorption or azeotropic distillation. The reaction mass is then cooled to ambient temperature. The unexpected effect of inducing crystallization of the acid salt was found upon such rigorous drying and controlled cooling of the reaction mass. In some instance, crystallization of the acid salt is induced by slow and gentle heating of the reaction medium. Such slow and gentle heating was found to induce crystallization of the acid salt. The slurry is then cooled to less than or about 20° C. The crystalline benzphetamine acid salt is recovered by any suitable solid/liquid separation means such as filtration. The crystals are typically washed with a suitable organic medium such as ethyl acetate and dried.

In yet another aspect of this invention it has been found that crystallization of benzphetamine acid salt can be achieved at low water levels and higher temperatures when the amount of methamphetamine impurities have been lowered to a low level. Such higher temperatures are in the range of from 60° C. to about 100° C.

DETAILED DESCRIPTION OF INVENTION

The present invention includes a process whereby crude benzphetamine hydrochloride is purified and crystallized by the dispersion of the product in a liquid medium in which benzphetamine is essentially insoluble to form a biphasic mixture. Preferably, the liquid medium is an organic medium. By "essentially insoluble", it is meant that crude benzphetamine hydrochloride has a partition coefficient in a biphasic mixture of organic medium and water of less than about 0.1 in the organic medium. Preferably, the organic medium is capable of forming a water azeotrope. Accordingly, suitable organic mediums include xylene, toluene, ethyl acetate, heptane, cyclohexane and benzene. A preferred organic medium is toluene. Preferably, between about 200 grams to about 700 grams of crude benzphetamine is added per Liter of organic medium.

The addition of crude benzphetamine to the liquid medium yields a biphasic mixture. Accordingly, the biphasic mixture is vigorously agitated to disperse the crude benzphetamine into the liquid medium. Agitation can be accomplished by mechanical stirring, at for example, 120 rpm for a stirring paddle having a 2.5 ft radius for large scale preparations. For laboratory-scale preparations, agitations can be accomplished by mechanical stirring at about 500 to about 1200 rpm. The biphasic mixture is preferably agitated throughout azeotropic drying until water is removed by azeotropic drying so that no more than 0.11 wt % water remain, and the benzphetamine crystallizes and is ready for filtration or centrifugation.

Crystallization may occur during a cycle of heating and/or cooling depending on the starting temperature. In one embodiment, once the water is removed, the mixture is slowly cooled through the temperature range of from about 60° C. to about 40° C. If the starting temperature of the mixture is below about 60° C., the temperature of the mixture is slowly heated to above about 60° C., more preferably from about 60° C. to about 100° C., more preferably from about 60° C. to about 75° C. The mixture is then slowly cooled through the temperature range of from about 60° C. to about 40° C. If no crystallization of the benzphetamine acid salt is observed before the mixture cools to below 40° C., crystallization of the benzphetamine acid salt can be induced by repeating the heating/cooling cycle whereby the mixture is gently and slowly heated to a temperature in the range of from about 40° C. to about 80° C. Preferably, the temperature of the reaction mass is raised slowly over a period of from about 5 minutes to about 1,000 minutes. If the crystallization does not occur upon heating, the mixture is slowly cooled again through the temperature range of from about 60° C. to about 40° C. In some instances, when crystallization does not occur at this point, additional, fresh organic medium is added which is further removed by distillation.

The heating/cooling cycles are performed under atmospheric pressure in a nitrogen blanketed vessel open through a distillation column. The heated biphasic mixture may be cooled by, for example, applying a refrigerated liquid to a jacket surrounding the container holding the biphasic mixture. The heating/cooling cycles achieve purification of about 95% to about 99%, and the benzphetamine hydrochloride exhibits melting points between about 151° C. and about 158° C.

In an alternate embodiment, higher temperature crystallization of benzphetamine acid salt can be achieved when the amount of methamphetamine in the mixture is reduced to a low level. Methamphetamine is a typical contaminant of the product as a result of the most common methods of manufacture of the product. Such higher temperatures are in the range of from 60° C. to about 100° C., more preferably from about 70° C. to about 95° C.

Once crystallization has been induced the slurry is then cooled to a temperature below about 20° C. to provide maximum crystallization. After maximum crystallization has been induced the crystals of benzphetamine acid salt are separated from the organic medium by any convenient means. Typically, the crystals are removed by simple filtration followed by washing of the crystals with an appropriate medium such as ethyl acetate, toluene, benzene, xylene, petroleum ether and the like. Other means of filtration include but are not limited to vacuum filtration and centrifugation.

The purified benzphetamine hydrochloride may be separated from water by Dean-Stark azeotroping or rotary evaporation. The crystallized benzphetamine hydrochloride may be isolated from the organic medium by filtration or centrifugation followed by rinsing and drying.

An important discovery in the process of this invention is that the presence of even small amounts of water such as about 0.16% in an organic medium containing the benzphetamine acid salt inhibits crystallization of the acid salt from the organic medium. Accordingly, the first steps taken in the process of this invention are to remove even traces of water from the organic medium containing benzphetamine acid salt. Any suitable means for removing water is therefore the first step or steps in the operation of the process of this invention. For example, a common means to remove water is by means of a rotary evaporator. However, in most cases such means does not remove water to the very low levels now discovered to be required for convenient crystallization of benzphetamine salt. Although not preferred, water can be removed without need for introducing an organic medium in a process (with or without reduced pressure) wherein only heat is applied to the benzphetamine acid salt. Temperatures in excess of 100° C. are typically employed in the absence of an organic medium.

In one aspect of the invention, the first step of the present process is to remove as much water as can be removed by simple distillation employing any suitable means. Typically, a Dean-Stark Trap is employed to collect a major amount of water. However, it has been discovered that a very small amount of water inhibits crystallization. Accordingly, water is removed from the benzphetamine salt employing an organic medium, typically toluene, to an amount below about 0.11%, by weight, preferably below about 0.09%, by weight and more preferably below about 0.02%, by weight.

Another convenient means to remove water from the system containing benzphetamine acid salt is the use of drying agents such as zeolites, magnesium sulfate, calcium chloride and the like. Further, water may be removed by typical standard operations such as spray drying.

Alternatively, a method for removing such small amounts of water retained in the organic medium is by means of azeotropic distillation of an organic medium. The mixture containing benzphetamine acid salt oil and organic medium is typically subjected to azeotropic distillation to remove free water while recycling the dry medium to the distillation vessel until the free water is eliminated and then removing up to about 80% of the toluene, by volume. Fresh, dry toluene is then added back in an amount to replace the volume that was removed by distillation. Typically it is sufficient to remove an amount of organic medium in the range of from about 40% to about 100%, by volume. Such added dry toluene is then further distilled thus continuing the lowering of water content in the benzphetamine acid salt. In the method of drying and crystallization that uses toluene azeotrope, a significant benefit may be achieved by agitating the toluene and benzphetamine acid salt oil mixture. Aggressive stirring can generate smaller suspended droplets of the oil, which when crystallized, excludes more impurities and form smaller and rounder particles of crystallized benzphetamine acid salt. The result is a higher purity and better flowing solid.

In another process of the present invention, water is removed from crude benzphetamine acid salt upon heating to a temperature above approximately 100° C., more preferably, above 110° C.

One of the advantages of the process of this invention is the purification of benzphetamine acid salt. It has been found that impurities such as benzyl chloride and its by-products remain in the organic medium thereby improving the color and purity of the desired products.

While this invention is described utilizing the hydrochloride salt, it should be understood that any suitable acid salt can be employed such as other halide acid salts, and acid salts derived from any suitable acid.

In the following examples and claims, percentage figures represent percent by weight.

Example 1

Benzphetamine hydrochloride is prepared in typical fashion in toluene. After reaction of methamphetamine with benzyl chloride in the presence of sodium carbonate, the reaction mass contained 28.76 g (0.1202 mole) of the acid salt which was a yield of 82.5%. To the reaction mass were added 100 g of deionized water. The mixture was stirred to dissolve the salts and then transferred to a separatory funnel. The reaction flask was rinsed with 50 g of water and 65 g of toluene. The rinsings were added to the separatory funnel. The layers were separated into a 169.5 g water layer and a 104.2 g of organic layer. The water layer was extracted twice with 27 g portions of toluene. The organic layers were combined bringing the total amount of organic medium to 156.1 g. The combined toluene portions were then washed with 33 g of deionized water.

The extraction step described in this paragraph and other following examples are set forth and claimed in co-pending provisional application entitled "Process for the Purification of Benzphetamine Hydrochloride", U.S. Prov. Ser. No. 60/630,008, filed Nov. 22, 2004. Unreacted methamphetamine in the washed toluene layer was extracted with water. The methamphetamine resulted from the reaction forming benzphetamine and was carried forward in the toluene. The extraction was carried out with 75 g of deionized water while stirring in 1.86 g (0.0294 mole) of 37.5% hydrochloric acid. The resulting pH of the water layer was 5.5. The pH of the water layer was adjusted to 6.3 by adding 5.05 g (0.0060 mole) of 10% sodium bicarbonate solution. The 80 g of water layer was separated and analysis showed that it contained 5.4% (4.32 g, 0.0232 mole) of methamphetamine hydrochloride and 0.076% (0.0608 g, 0.00022 mole) of benzphetamine hydrochloride. Analysis showed that the extracted toluene layer contained 0.156%, by weight, of methamphetamine hydrochloride and 19.95% (31.14 g, 0.1129 mole) benzphetamine hydrochloride. This result indicates an 83% yield based on the initial methamphetamine after adjusting for the 6.6%, of samples that were taken during the benzylation step.

The extracted toluene solution was acidified by adding 12.85 g of 37.5% hydrochloric acid providing a pH of 1. The mass was transferred to a 500 ml three-neck flask fitted with a Dean-Stark Trap, condenser and mechanical stirrer. The separatory funnel was rinsed with 27.1 g of water, which was added to the three-neck flask for a total weight of 182 g. There contents of the flask were distilled whereby 34.3 g of water and 96.8 g of toluene were distilled forward. Then 86.2 g of fresh toluene were added to the flask and 74.7 g of toluene distilled forward. The resulting mass weighed 59 g. This mass did not produce crystals when cooled to ambient temperature. Upon re-heating slowly to 50° C. there was observed rapid crystallization. The mass was vacuum filtered and the crystals were washed with 31 g (35 ml) of fresh toluene. There was obtained a 31.77 g wet cake which was dried in a vacuum oven to provide 26 g of a tan colored benzphetamine hydrochloride powder having a melting point of 151.2-154.1° C. After adjusting for samples that were taken, there was a 70.7% yield based on the initial amount of methamphetamine. The dried crude crystals contained about 0.1%, by weight, methamphetamine hydrochloride, 93.5%, by weight, of benzphetamine hydrochloride and 0.6%, by weight toluene.

The dried crude benzphetamine hydrochloride was recrystallized by dissolving 23.25 g in 106 g of 15.7% isopropanol in ethyl acetate mixed solvent. The 80 g of the mixed solvent was distilled from the flask and 86.8 g of fresh ethyl acetate was added to the pot oil resulting in an immediate crystallization. The mixture was immersed into an ice bath for one hour and then vacuum filtered. The crystals were washed with 61 g of ethyl acetate to provide 21.33 g of wet cake. The crystals were dried in a vacuum oven at 53° C. and 19 inches of Hg with a nitrogen purge for one hour providing 20.73 g of purified benzphetamine. The recrystallized product indicates a more pure product than that reported in the '138 patent mentioned above by a comparison of the melting point which was 154.5-158° C. compared to 129-130° C. reported in the '138 patent. An HPLC analysis of the recrystallized product found 98.1%, by weight, benzphetamine hydrochloride and 0.03%, by weight, methamphetamine hydrochloride.

Example 2

A sample of crude benzphetamine hydrochloride produced in a typical process employing methamphetamine, benzyl chloride in the presence of sodium carbonate was stripped using a rotary evaporator at about 7 torr and a temperature of up to 86° C. The dried product did not crystallize but formed an oil. The oil was further dried using a heat gun to achieve a higher temperature. Another 13.6% of mass, mostly water, was distilled forward and the resulting oil readily crystallized as the mass cooled.

Examples 3-8

Additional crystallization procedures were carried out by the process of this invention as described in Example 1 and the product of each example subjected to HPLC analysis. The amounts of materials involved in each example, the amount of product as well as the results of the analysis are summarized in Table 1 below. In these examples and in Table 1, the percent shown is percent by weight.

In each example, benzphetamine was synthesized by the reaction of methamphetamine base and benzyl chloride in toluene in the presence of sodium carbonate to neutralize the by-product hydrochloride acid. The reaction was carried out at 120° C. The reaction mixture was treated with deionized water and toluene to dissolve the salts and separate them from the reaction products. Aqueous layers from the separations were extracted twice with toluene, and the three toluene layers from each batch were combined and then washed with deionized water.

Un-reacted methamphetamine was extracted from the combined toluene layers in a separatory funnel by adding deionized water and 37% hydrochloric acid with vigorous mixing to provide contact between the two phases. In examples 3 and 4 the final aqueous phase pH was below the targeted range of 6 to 7, resulting in lower yields of crude benzphetamine hydrochloride. In other examples, a 5% solution of sodium hydroxide was added as necessary to adjust the final aqueous phase to a pH of about 6.

The aqueous phases from the above extractions were discarded and the organic phases were acidified to a pH of about 1 with 37.5% hydrochloric acid. The acidified mixtures were then transferred to a 2 L three-neck flask, equipped with a nitrogen inlet, mechanical stirrer, a Dean-Stark Trap and a cold water condenser. The flask was heated under a 20 sccm nitrogen purge until the toluene-water mixture began distilling over at a temperature of 88° C. with water being collected in the trap and the toluene returned to the distillation vessel. The distillation was continued until no more water collected at which point the flask temperature was 111° C. Toluene was distilled forward and drained from the trap until 70 to 80% of the toluene in the acidified mixture had been removed.

The concentrated mixtures were cooled with stirring to less than 80° C. before fresh toluene was added to the flask. The mixtures were then reheated, and in all examples benzphetamine hydrochloride began to crystallize at a temperature between 73° C. and 95° C. Heat was removed as soon as solids were observed and the slurries were cooled to less than 25° C. before filtering. The filtered solids were washed with toluene and in some cases a second wash with cold ethyl acetate. The wet solids were then dried overnight in a vacuum oven at 60° C.

The yield of crude benzphetamine hydrochloride from methamphetamine in these examples varied between 69% and 90% with the higher (85% to 90%) yields obtained when the aqueous phase pH in the methamphetamine extraction step was at or below 6. After drying, the product was a free-flowing white crystalline solid. HPLC analyses indicated that the greatest amount of impurity was toluene at 0.02% to 0.32% with little or no methamphetamine or dibenzylamphetamine detected.

TABLE 1

| | Example No. | | | | | | |
|---|---|---|---|---|---|---|---|
| | 3 | 4 | 5 | 6 | | 7 | 8 |
| | | | | (a) | (b) | | |
| Initial methamphetamine base (g) | 116.61 | 91.15 | 201.00 | 305.00 | | 155.16 | 153.21 |
| Extraction of toluene layers | | | | | | | |
| Combined toluene layers (g) | 560.5 | 442.2 | 927.8 | 1425.2 | | 723.9 | 733.7 |
| Deionized water (g) | 402.8 | 315.2 | 693.0 | 500.0 | | 330.0 | 330.0 |
| Hydrochloric acid (g) | 15.6 | 11.2 | 7.2 | 21.2 | | 7.7 | 6.3 |
| Sodium bicarbonate (g) | 0.0 | 0.0 | 0.0 | 15.0 | | 19.2 | 7.9 |
| Aqueous phase discarded (g) | 432.5 | 147.7 | 718.4 | 543.4 | | 363.2 | 352.5 |
| Aqueous phase pH | 5.5 | 5.1 | 6.1 | 6.0 | | 6.1 | 6.3 |
| Acidification of Organic Phase | | | | | | | |
| Organic phase (g) | 544.4 | 421.1 | 909.6 | 698.6 | 706.2 | 717.6 | 725.5 |
| Wash water) g) | 42.3 | 0.0 | 12.3 | 18.2 | 0.0 | 0.0 | 0.0 |
| Wash toluene (g) | 11.9 | 0.0 | 0.0 | 5.8 | 21.3 | 0.0 | 0.0 |
| Hydrochloric acid (g) | 63.4 | 48.9 | 127.3 | 92.6 | 93.9 | 99.5 | 99.1 |
| Distillation and crystallization | | | | | | | |
| Wash water (g) | 60.0 | 15.6 | 205 | 203.0 | 179.0 | 181.0 | 180.4 |
| Added toluene (g) | 238.5 | 0.0 | 0.0 | 0.0 | 0.0 | 0.0 | 0.0 |
| Estimated total Toluene (g) | 648 | 333 | 605 | 486 | 507 | 485 | 494 |
| Estimated Total water (g) | 142 | 46 | 298 | 280 | 238 | 244 | 243 |
| Aqueous phase distilled (g) | 156 | 52 | 300 | 280 | 240 | 243 | 244 |
| Toluene distilled (g) | 514 | 236 | 421 | 368 | 372 | 363 | 381 |
| Toluene distilled (%) | 79 | 71 | 70 | 76 | 73 | 75 | 77 |
| Fresh toluene added (g) | 361 | 160 | 257 | 351 | 361 | 370 | 370 |
| Crystallization onset (° C.) | 75 | 90 | 95 | 93 | 76 | 73 | 75 |
| Crude Product Recovery | | | | | | | |
| Toluene wash (g) | 262.1 | 214.9 | 304.4 | 255.5 | 252.2 | 249.0 | 251.0 |
| Ethyl acetate wash (g) | none | none | none | 250.0 | 250.0 | 252.0 | 251.0 |
| Benzphetamine HCl after drying (g) | 152.8 | 116.2 | 314.7 | 241.1 | 247.2 | 258.8 | 255.1 |
| Yield from methamphetamine (%) | 71 | 69 | 85 | 86 | 87 | 90 | 90 |
| Crude Product HPLC Analysis (wt %) | | | | | | | |
| Methamphetamine | 0.00 | 0.01 | 0.00 | 0.00 | 0.00 | 0.00 | 0.00 |
| Benzphetamine HCl | 98.01 | 100.73 | 100.63 | 96.98 | 99.48 | 98.71 | 97.42 |
| Benzyl chloride | 0.00 | 0.00 | 0.02 | 0.00 | 0.00 | 0.00 | 0.00 |
| Toluene | 0.32 | 0.06 | 0.02 | 0.0 | 0.10 | 0.12 | 0.09 |
| Dibenzylamphetamine | 0.00 | 0.00 | 0.00 | 0.04 | 0.00 | 0.00 | 0.00 |
| Benzylpropylhexedrine | 0.00 | 0.00 | 0.06 | 0.10 | 0.00 | 0.11 | 0.04 |

Example 9

To a 100 ml 3-neck flask fitted with a mechanical stirrer was added 17.10 g (0.1145 moles) of methamphetamine, 14.50 g (0.1368 mole) of sodium carbonate and 10.60 g of toluene. The reaction mass was heated to 120° C. and 16.18 g (0.1265 mole) of benzyl chloride was added over 180 minutes. The reaction was continued for a total of 6.75 hr. The reaction mass was cooled and transferred to a 500 ml flask equipped with a mechanical stirrer. To this flask was added 45 ml of toluene and 90 ml of water. The mixture was aggressively stirred to dissolve the salt. The layers were separated and the water layer was washed twice with 20 ml portions of toluene. The combined toluene layers were washed with 20 ml of water. Then to the stirred toluene layer was added 11.33 g of concentrated hydrochloric acid. The flask was equipped with a Dean-Stark trap and condenser and the water was removed by azeotropic distillation. There was 8.9 g of water recovered from the Dean-Stark trap. The organic material crystallized upon cooling between about 60° C. to about 40° C. affording 19.79 g of crude benzphetamine hydrochloride which is a 70% yield.

Example 10

To a 100 ml 3-neck flask was added 25.07 g (0.1680 mole) of methamphetamine, 24.26 g (0.2289 mole) of sodium carbonate and 13.58 g of toluene. The mixture was stirred and heated to 120° C. Then 23.04 g (0.1820 mole) of benzyl chloride was added over 53 minutes. The reaction was continued for a total of 12 hr. After the reaction was completed the mixture was cooled to ambient temperature and 75 g of toluene and 150 g of water were added. After aggressively mixing the layers were separated and the water layer was washed twice with 30 ml portions of toluene. To the combined toluene layers was added 12.04 g of concentrated hydrochloric acid affording a pH of 1 in the water layer. The entire mixture was transferred to a 500 ml 3-neck flask fitted with a mechanical stirrer, Dean-Stark trap and condenser. The water was removed by azeotropic distillation. The benzphetamine hydrochloride crystallized upon cooling 60° C. to about 40° C. Filtration afforded 28.34 g (0.1027 mole) of benzphetamine HCl which is a 61% yield. The benzphetamine HCl had a melting point of 150.3-152.4° C.

Example 11

To a 250 ml three-neck flask was added 17.92 g (0.120 mole) of methamphetamine and 11.31 g of toluene. To this was added 14.72 g (0.1389 mole) of sodium carbonate powder. The mixture was mechanically stirred and heated to 105° C. Then 15.69 g (0.124 mole) of benzyl chloride was added drop wise over a period of 20 minutes. The reaction was exothermic and self-heated to 115° C. After the benzyl chloride addition was completed the reaction mass was heated to 120° C. and held at that temperature for seven hours. The reaction mass was cooled to 70° C. and 100 ml of deionized water was added. The water addition decreased the mass temperature to 35° C. The mixture was vigorously stirred for 10 minutes to dissolve the salts. Then 50 ml of toluene was added. The mixture was vigorously stirred for 15 minutes. The layers were separated affording a 116.5 g lower aqueous layer and an 82.99 g upper organic layer. The aqueous layer was extracted twice with 20 ml portions of toluene. The combined toluene layers weighed 112.21 g. The combined toluene layer was washed with 20 ml of deionized water. Then the toluene layer was transferred to the 250 ml three-neck flask and 12.05 g of 37.5 wt % hydrochloric acid (0.124 mole) was added with vigorous agitation. Agitation was continued for 20 minutes. Then the 127.7 g of reaction mass was concentrated on a rotary evaporator at reduced pressure provided by an aspirator using ice water and with the reaction mass heated to 40-70° C. using a water bath. There was obtained 31.48 g of an amber colored oil. To the oil was added 42 ml (38.23 g) of ethyl acetate. This was stirred and heated to 70° C. for 2.5 hours. No crystals formed upon cooling. The mixture was seeded with 0.003 g of benzphetamine hydrochloride crystals. Crystals formed over a period of 60 hours. The mixture was filtered and the filter cake was dried affording 8.99 g (0.0326 mole) of benzphetamine hydrochloride crystals. The melting point was 151.1-155° C. A 1.02 g sample of the benzphetamine hydrochloride crystals was recrystallized from 7.64 g of ethyl acetate and 1 g of isopropanol by heating to 68° C. to dissolve the crystals, filtering and cooling. There was a small amount of crystals isolated that had a melting point of 154.8-155.1° C. Analysis of the crystals found 99.4 wt % benzphetamine hydrochloride and 0.6 wt % methamphetamine.

Example 12

Methamphetamine base (60.0 grams) was transferred to a 250 mL 3-neck flask. The flask was fitted with a mechanical stirrer, a thermometer adapter and thermometer, and a dropping funnel. Anhydrous Na2CO3 (47.06 g) was added, forming a thick cake on the bottom of the flask. To dissolve the thick cake, toluene (36.35 g) was added, and the solution was stirred and heated to 95° C.

Benzyl chloride was added (51.17 g, 0.4042 moles, from Aldrich, Batch 13804-TA) drop wise, which caused an exothermic reaction, raising the temperature rapidly to 140° C. Addition was suspended, and the flask was cooled in a water bath and stirred for 30 minutes before addition resumed. It took 45 minutes to add all benzyl chloride.

The flask was heated to 105° C. for 6 hours and then cooled to ambient. 2.11 grams was taken for analysis. The flask was then reheated to 105° C. and maintained at this temperature for 3 hours, and then cooled to ambient temperature. DI water (200 mL) was added drop wise.

In the flask, the organic and aqueous layers separated. The organic layer containing crude benzphetamine was transferred to 500 mL 3-neck flask, and the aqueous layer was transferred to a separatory funnel. Toluene (48.4 g) was added to the separatory funnel, and the funnel was vigorously shaken. When the layers separated, the organic layer was transferred to the 500 mL 3-neck flask. Additional toluene (33.95 g) was added to the separatory funnel, which was shaken, and again the organic layer was transferred to 500 mL 3-neck flask.

To the 3-neck flask containing the organic layer was added 37% HCl (47.5 g) drop wise. The solution was stirred for 30 minutes and transferred to 1 L RB flask. The mixture was concentrated by rotary evaporation at temperature between 52 and 86° C. and pressure of 30 Torr. The total solution which weighed 256.18 grams was reduced to 92.70 g of crude benzphetamine hydrochloride, which was a viscous oil at temperatures below 70° C. 0.2448 g of the product was taken and diluted with 9.78 g DI water for analysis.

Two months later, the crude benzphetamine hydrochloride oil (which now weighed 103.62 grams) was charged to a 1 L RB flask and immersed in a hot water bath. The crude oil was heated to 78° C. Ethyl acetate (350 mL) was added to the flask, and the mixture was heated to 75° C. Most of the oil dissolved in the solvent, but the solution remained hazy. Heating was discontinued. Crystallization did not occur.

It was thought that water had become a major impurity in the crude sample, so the sample was next subjected to rotary evaporation. During evaporation, the sample was heated with a heat gun at 80° C. and vacuumed to a pressure of 30 Torr. The weight of the crude sample was reduced from 103.62 grams to 89.63 grams by rotary evaporation.

Ethyl acetate (400 mL) was added to the dried sample, and the solution was refluxed and stirred until it became clear. As soon as the flask was removed from heat, the solution became hazy. The sample was allowed to cool, and as it cooled, crystals began to form. After it reached ambient temperature, the flask was immersed in an ice bath and cooled to 6° C.

After filtration, the solid cake and stir bar (75.42 grams) was dried in a vacuum oven at 60° C. at 30 Torr for 2 hours, leaving 75.11 g of powdered benzphetamine hydrochloride. After removal of the stir bar from the cake, the actual recovered purified benzphetamine hydrochloride sample weighed 68.12 grams, representing a 76% recovery. A sample was tested for purity by melting point determination. Its melting point range was 153.5 to 154.5° C., indicating a high purity product. The total yield from the synthesis was 59.8% based on the starting material ephedrine.

Although the invention has been described by the above examples, such examples have been chosen to illustrate rather than limit the scope of the invention as defined by the following claims.

The invention claimed is:

1. A process for preparing a crystalline form of benzphetamine hydrochloride comprising:

(a) dispersing a crude benzphetamine hydrochloride in an organic medium in which benzphetamine hydrochloride is essentially insoluble to form a biphasic mixture comprising the crude benzphetamine hydrochloride and the organic medium, the biphasic mixture containing an amount of water;

(b) contacting the biphasic mixture with a drying agent to remove water from the crude benzphetamine hydrochloride and to lower the water content of the biphasic mixture to less than about 0.11% by weight;

(c) crystallizing the benzphetamine hydrochloride product from (b); and (d) separating the crystalline benzphetamine hydrochloride from the organic medium.

2. The process of claim 1 wherein the organic medium is selected from the group consisting of xylene, toluene, ethyl acetate, heptane, cyclohexane and benzene.

3. The process of claim 2 wherein the organic medium is toluene.

4. The process of claim 1 wherein the organic medium is a reaction medium in which the crude benzphetamine hydrochloride is produced.

5. The process of claim 1 wherein crystallizing the benzphetamine hydrochloride comprises cooling the biphasic mixture through the temperature range of from about 60° C. to about 40° C.

6. The process of claim 1 wherein crystallizing the benzphetamine hydrochloride comprises cooling the biphasic mixture through the temperature range of from about 60° C. to about 40° C. and then heating the biphasic mixture to a temperature above about 40° C.

7. The process of claim 6 wherein the biphasic mixture is heated to a temperature between about 40° C. to about 100° C.

8. The process of claim 1 wherein crystallizing the benzphetamine hydrochloride comprises heating the biphasic mixture to a temperature between about 40° C. and about 100° C.

9. The process of claim 8 wherein crystallizing the benzphetamine hydrochloride further comprises cooling the biphasic mixture to precipitate the crystalline benzphetamine hydrochloride.

10. The process of claim 1 wherein the crystalline benzphetamine hydrochloride is separated from the organic medium by filtration.

11. The process of claim 1 wherein the drying agent is selected from the group consisting of zeolites, magnesium sulfate and calcium chloride.

12. The process of claim 1 wherein the water content of the biphasic mixture is lowered to less than about 0.09%.

13. The process of claim 1 wherein the water content of the biphasic mixture is lowered to less than about 0.02%.

14. The process of claim 1 wherein the crude benzphetamine hydrochloride contains methamphetamine, and further wherein the crystalline benzphetamine hydrochloride contains less methamphetamine than the crude benzphetamine hydrochloride.

15. The process of claim 14 wherein the benzphetamine hydrochloride crystallizes at a temperature in the range of from about 70° C. to about 95° C.

16. A process for preparing a crystalline form of benzphetamine hydrochloride comprising:

(a) dispersing a crude benzphetamine hydrochloride in an organic medium in which benzphetamine hydrochloride is essentially insoluble to form a biphasic mixture comprising the crude benzphetamine hydrochloride and the organic medium, the biphasic mixture containing an amount of water;

(b) removing water from the biphasic mixture by use of a drying agent or by azeotropic distillation of the organic medium;

(c) removing up to about 80%, by volume, of the organic medium by distillation;

(d) adding fresh organic medium to the mixture;

(e) crystallizing the benzphetamine hydrochloride product from (d); and (f) isolating the crystalline benzphetamine hydrochloride by means of solid\liquid separation.

17. The process of claim 16 wherein the organic medium is toluene.

18. The process of claim 16 wherein the organic medium is ethyl acetate.

19. The process of claim 16 wherein the organic medium is the reaction medium in which the crude benzphetamine hydrochloride is produced.

20. The process of claim 16 wherein the solid\liquid separation is by means of filtration.

21. The process of claim 16 wherein the solid\liquid separation is by means of centrifugation.

22. The process of claim 18 wherein the solid\liquid separation is by means of vacuum filtration.

23. The process of claim 16 wherein step (d) further comprises distilling the fresh organic medium from the mixture.

24. A process for preparing a crystalline form of benzphetamine hydrochloride comprising:

(a) dispersing a crude benzphetamine hydrochloride in an organic medium in which benzphetamine hydrochloride is essentially insoluble to form a biphasic mixture comprising the crude benzphetamine hydrochloride and the organic medium, the biphasic mixture containing an amount of water;

(b) removing water from the crude benzphetamine hydrochloride in the biphasic mixture by azeotropic distillation of the organic medium to lower the water content of the biphasic mixture to less than about 0.11% by weight;

(c) crystallizing the benzphetamine hydrochloride product from (b); and (d) separating the crystalline benzphetamine hydrochloride from the organic medium.

25. The process of claim 24 wherein the organic medium is selected from the group consisting of xylene, toluene, ethyl acetate, heptane, cyclohexane and benzene.

26. The process of claim 25 wherein the organic medium is toluene.

27. The process of claim 24 wherein the organic medium is a reaction medium in which the crude benzphetamine hydrochloride is produced.

28. The process of claim 24 wherein crystallizing the benzphetamine hydrochloride comprises cooling the biphasic mixture through the temperature range of from about 60° C. to about 40° C. and then heating the biphasic mixture to a temperature above about 40° C.

29. The process of claim 24 wherein crystallizing the benzphetamine hydrochloride comprises heating the biphasic mixture to a temperature between about 40° C. and about 100° C. and cooling the biphasic mixture to precipitate the crystalline benzphetamine hydrochloride.

30. The process of claim 24 wherein the water content of the biphasic mixture is lowered to less than about 0.09%.

31. The process of claim 24 wherein the water content of the biphasic mixture is lowered to less than about 0.02%.

* * * * *